US009381238B2

(12) United States Patent
Terrier et al.

(10) Patent No.: US 9,381,238 B2
(45) Date of Patent: Jul. 5, 2016

(54) METHOD FOR IMPROVING THE PRODUCTION OF INFLUENZA VIRUSES AND VACCINE SEEDS

(75) Inventors: Olivier Terrier, St Andrews (GB); Jean-Christophe Bourdon, Dundee (GB); Manuel Rosa-Calatrava, Lyons (FR)

(73) Assignees: UNIVERSITY OF DUNDEE, Dundee (GB); CENTRE NATIONAL DE LA RECHERCHE SCIENTIFIQUE, Paris (FR); UNIVERSITE CLAUDE BERNARD LYON I, Villeurbanne (FR); HOSPICES CIVILS DE LYON, Lyons (FR)

( * ) Notice: Subject to any disclaimer, the term of this patent is extended or adjusted under 35 U.S.C. 154(b) by 92 days.

(21) Appl. No.: 13/883,310

(22) PCT Filed: Nov. 4, 2011

(86) PCT No.: PCT/FR2011/052575
§ 371 (c)(1),
(2), (4) Date: Jul. 15, 2013

(87) PCT Pub. No.: WO2012/059696
PCT Pub. Date: May 10, 2012

(65) Prior Publication Data
US 2013/0315954 A1 Nov. 28, 2013

(30) Foreign Application Priority Data
Nov. 5, 2010 (FR) ...................................... 10 59132

(51) Int. Cl.
*A61K 39/145* (2006.01)
*C12N 7/00* (2006.01)
*A61K 39/12* (2006.01)

(52) U.S. Cl.
CPC .............. *A61K 39/145* (2013.01); *A61K 39/12* (2013.01); *C12N 7/00* (2013.01); *C12N 2760/16051* (2013.01); *C12N 2760/16151* (2013.01)

(58) Field of Classification Search
None
See application file for complete search history.

(56) References Cited

U.S. PATENT DOCUMENTS

| | | | |
|---|---|---|---|
| 6,617,346 B1 | 9/2003 | Kong et al. | |
| 6,734,302 B2 | 5/2004 | Kong et al. | |
| 7,060,713 B2 | 6/2006 | Kim et al. | |
| 7,115,598 B2 | 10/2006 | Lu et al. | |
| 7,495,007 B2 | 2/2009 | Chen et al. | |
| 7,514,579 B2 | 4/2009 | Khan et al. | |
| 7,576,082 B2 | 8/2009 | Luk et al. | |
| 2003/0153580 A1 | 8/2003 | Kong et al. | |
| 2004/0142450 A1 | 7/2004 | Seo et al. | |
| 2006/0188977 A1 | 8/2006 | Schwartz et al. | |
| 2006/0211693 A1 | 9/2006 | Fotouhi et al. | |
| 2007/0129416 A1 | 6/2007 | Ding et al. | |
| 2007/0167437 A1 | 7/2007 | Fotouhi et al. | |
| 2008/0004287 A1 | 1/2008 | Ma et al. | |
| 2008/0081810 A1 | 4/2008 | Chen et al. | |
| 2008/0138362 A1 | 6/2008 | Mochizuki | |
| 2008/0255119 A1 | 10/2008 | Dominique et al. | |
| 2008/0262200 A1 | 10/2008 | Nash | |
| 2008/0280769 A1 | 11/2008 | Doemling | |
| 2008/0293723 A1 | 11/2008 | Lieu et al. | |
| 2009/0008553 A1 | 1/2009 | Robbins et al. | |
| 2009/0068144 A1 | 3/2009 | Weber et al. | |
| 2009/0149493 A1 | 6/2009 | Lacrampe et al. | |
| 2009/0306130 A1 | 12/2009 | Weber et al. | |
| 2010/0062489 A1 | 3/2010 | Guehenneux et al. | |
| 2010/0125064 A1 | 5/2010 | Boettcher et al. | |
| 2010/0197010 A1 | 8/2010 | Erbs et al. | |
| 2011/0053937 A1 | 3/2011 | Lacrampe et al. | |
| 2011/0294209 A1 | 12/2011 | Pain et al. | |
| 2012/0071508 A1 | 3/2012 | Lacrampe et al. | |

FOREIGN PATENT DOCUMENTS

| | | |
|---|---|---|
| EP | 0 947 494 | 10/1999 |
| EP | 1 739 167 | 1/2007 |
| EP | 1 996 591 | 12/2008 |
| WO | 03/041715 | 5/2003 |
| WO | 2006/091646 | 8/2006 |
| WO | 2008/130614 | 10/2008 |
| WO | 2009/142450 | 11/2009 |

OTHER PUBLICATIONS

Tovar et al. Small-molecule MDM2 antagonists reveal aberrant p53 signaling in cancer: implications for therapy. Proc Natl Acad Sci U S A. Feb. 7, 2006;103(6):1888-93. Epub Jan. 27, 2006.*
Shehata et al. Influenza Vaccination in Cancer Patients Undergoing Systemic Therapy. Clin Med Insights Oncol. 2014; 8: 57-64.*
Saha et al. Targeting p53 by small molecules in hematological malignancies. J Hematol Oncol. Mar. 27, 2013;6:23. doi: 10.1186/1756-8722-6-23.*
Lipatov et al. Neurovirulence in mice of H5N1 influenza virus genotypes isolated from Hong Kong poultry in 2001. J Virol. Mar. 2003;77(6):3816-23.*
Jennings et al. Stockpiling prepandemic influenza vaccines: a new cornerstone of pandemic preparedness plans. Lancet Infect Dis. Oct. 2008;8(10):650-8. doi: 10.1016/S1473-3099(08)70232-9.*
Lu et al., "Discovery of . . . Screening Strategy", J. Med. Chem. 2006, 49, 3759-3762.
Nicholls et al., "Tropism of . . . Respiratory tract", Nature Medicine, vol. 13, No. 2, Feb. 2007.
Enami et al., "Introduction of . . . influenza virus", Proc. Natl. Acad. Sci. USA, vol. 87, pp. 3802-3805, May 1990.
Vassilev et al., "In Vivo Activation . . . Antagonists of MDM2", Science 303, 844 (2004).

(Continued)

*Primary Examiner* — Nick Zou
(74) *Attorney, Agent, or Firm* — Clark & Brody

(57) ABSTRACT

The present invention relates to a method for improving the production of an influenza virus, and in particular influenza vaccine seeds, or a vaccine directed against an influenza virus, characterized in that the production is carried out in the presence of an inhibitor of the interaction between the Mdm2 protein and the p53 protein.

17 Claims, 4 Drawing Sheets

(56) References Cited

OTHER PUBLICATIONS

Riel et al., "H5N1 Virus . . . Respiratory Tract", Science. vol. 312, Apr. 21, 2006.
Rothweiler et al., "Isoquinolin-1-one . . . MDM2-p53 Interaction", www.chemmedchem.org, ChemMedChem 2008, 3, 1118-1128.
Klein et al., "Targeting the . . . treat cancer", British Journal of Cancer (2004) 91, 1415-1419.
Shangary et al., "Small-Molecule . . . Cancery Therapy", Annu. Rev. Pharmacol. Toxicol. 2009, 49: 223-241.
Stoll et al., "Chalcone Derivatives . . . MDM2 and p53", Biochemistry 2001, 40, 336-344.
Weber, Patented inhibitors . . . interaction (2006-2008), NexusPharma, Inc., Review.
Hampson et al., Special Edition Editorial, Journal Compilation, 2008, Blackwell Publishing Ltd., Influenza and Other Respiratory Viruses, 2, 191-192.
Ding et al., "Structure-Based . . . MDM2-p53 Interaction", J. Med. Chem. 2006, 49, 3432-3435.
Luytjes et al., "Amplification, Expression . . . Influenza Virus", Cell, vol. 59, 1107-1113, Dec. 22, 1989.
Le Ru et al., "Scalable production . . . vaccine manufacturing", Vaccine 28, (2010) 3661-3671.
Kane et al., "Development of . . . Time-Resolved Fluorescence", Analytical Biochemistry 278, 29-38 (2000).
Bottger et al., "Design of a . . . response in vivo", Research Paper, Current Biology, vol. 7, No. 11, Oct. 17, 1997.
Enami et al., "High-Efficiency . . . Virus Transfectants", Journal of Virology, May 1991, p. 2711-2713.
Hoffmann et al., "Unidirectional RNA . . . eight plasmids", Journal of General Virology (2000), 81, 2843-2847.
U.S. Appl. No. 60/781,958, filed Mar. 13, 2006, Liu et al.
XP002635306; Mar. 19, 2009, Duan, Ming et al. Database accession No. 2009:330316.
Lietzen et al., "Quantitative Subcellular . . . Primary Macrophages", PLoS Pathogens, May 2011; 7(5): e1001340, pp. 1-13.
Coombs et al., "Quantitative Proteomic . . . Human Lung Cells", Journal of Virology, Oct. 2010; 84(20) : pp. 10888-10906.
Turpin et al., "Influenza Virus . . . Viral Replication", Journal of Virology, Jul. 2005; 79 (14) : pp. 8802-8811.
Terrier et al., "Cellular transcriptional . . . p53 pathway", Virology Journal, Jun. 8, 2011, 8:285, pp. 1-11.

\* cited by examiner

A549 cells - H3N2 A/Moscow/10/99 virus

A549 cells - H3N2 A/Moscow/10/99 virus

A549 cells - H3N2 A/Moscow/10/99 virus

A549 cells - H3N2 A/Moscow/10/99 virus

MDCK cells - H3N2 A/Moscow/10/99 virus

A549 cells - H3N2 A/Moscow/10/99 virus

A549 cells - H3N2 A/Moscow/10/99 virus

METHOD FOR IMPROVING THE PRODUCTION OF INFLUENZA VIRUSES AND VACCINE SEEDS

The present invention relates to the technical field of influenza viruses and vaccine seeds. More specifically, the invention relates to methods for improving the production of influenza viruses and of influenza vaccine seeds.

The flu is a common viral respiratory infection seen throughout the world, which develops in epidemic episodes during the winter in temperate regions, due to influenza viruses. It remains in this day and age the second highest cause of infectious mortality after pneumonia. The influenza viruses responsible for pathological conditions in human beings are the influenza type A and B viruses. Although influenza type B viruses circulate in lineage form, influenza type A viruses are categorized into viral subtypes according to the antigenic properties of the two major surface glycoproteins, hemagglutinin (HA) and neuraminidase (NA). Influenza viruses have between 300 and 700 glycoproteins at their surface, associated with a theoretical NA/HA ratio of one-to-ten. The viruses circulating in human beings and responsible for seasonal epidemics are the A (H1N1) and A (H3N2) viruses. Since the main reservoir of influenza viruses is the animal (avian and porcine) reservoir, animal viruses can cross the species barrier and infect human beings. Viruses such as the highly pathogenic avian A (H5N1) virus and the A (H1N1) virus responsible for the pandemic in 2009 can cause serious public health problems.

Vaccination is, for the moment, the only effective means for protecting populations against influenza viruses. The "seasonal" vaccine makes it possible to acquire immunity against circulating seasonal A (H1N1) and A (H3N2) viruses and B viruses. It is defined each year by the WHO on the basis of the prototype strains of the previous year. The host's immune response is mainly of humoral type with the synthesis of neutralizing antibodies which are directed against the HA and NA proteins. Because of a considerable antigenic shift of these two proteins, in particular for the type A viruses, the vaccine composition must be reevaluated annually.

The culturing of influenza viruses constitutes a critical element in the field of vaccine production, but also in the field of fundamental and biomedical research on influenza viruses. Reassortant vaccine influenza viruses are mainly grown in the embryonated chicken egg system. It is currently estimated that one egg enables the production of one dose of trivalent vaccine (Hampson et al. Influenza Other Respi Viruses. 2008 Nov. 2(6), 191-2). The method for producing vaccine on eggs requires a timescale of from 5 to 6 months, which cannot be shortened. In order to face the increasing demand for vaccines against circulating seasonal strains, but also the demand—which is difficult to predict—for vaccines against one (or more) potentially pandemic emergent strains, the availability of eggs can prove to be a limiting factor, all the more so since risks of avian pandemics in poultry farms remain. In addition, the poultry themselves are capable of being affected by influenza viruses, which could cause supply difficulties if farms intended for virus production were themselves involved in an influenza virus pandemic. In this context and from an economic point of view, the search for and development of new optimized methods for producing vaccine seeds are legitimate (time reduction and/or cost reduction).

Alternative strategies for obtaining vaccine doses have been developed over the past few years. Indeed, the use of cell lines for amplifying vaccine reassortants makes it possible, inter alia, to no longer be dependent on the "egg" system (amount of eggs potentially insufficient for managing a pandemic), reduces the surface-antigen modifications regularly observed in allantoic production and would lead to fewer risks of allergy. However, at the current time, few manufacturers have chosen this new mode of production since the industrial process is far from being as effective as that in the allantoic system. Indeed, both the production of viruses and the production of viral antigens (HA and NA) in cell culture come up against difficulties in terms of yield and therefore of amount of viruses or of antigens produced. Many research teams are currently developing virus production cell systems in order to supplement or even replace the production-in-egg model. These cell systems are generally permissive for a greater number of viral strains than in the allantoic system and can be rapidly set up on an industrialization scale (Barrett et al. CurrOpinMolTher. 2010 February; 12(1):21-30). Furthermore, these systems can be coupled with reverse genetics techniques, which make it possible to produce recombinant viruses (vaccine seeds) in a rapid and flexible manner, which are also optimized for their virological properties (replication, antigen expression, etc.). For health safety and regulatory reasons, the cell lines chosen must be selected for their ability to produce virus with high titers, in synthetic media free of proteins of animal origin (synthetic media without serum of animal origin). Cell systems for production in cells in suspension have also been described (Le Ru et al. Vaccine. 2010 May 7; 28(21):3661-71). The cell lines which have regulatory authorizations, such as the MDCK, Vero, BHK21, CHO, HEK 293 and PERC6 lines, have not made it possible, to date, to obtain production yields which are adequate for manufacturers.

One of the major economic challenges is to be able to reduce the cost and the time taken to produce a vaccine dose (more doses per production and/or reduction in the time taken to obtain the same amount of doses).

The invention is based on the unexpected observation that an action which is antagonistic to the activity of Mdm2 and which more particularly inhibits the p53-Mdm2 interaction has an impact on the replicative cycle of influenza viruses.

In this context, the present invention provides a novel method for producing influenza viruses and vaccine seeds, characterized in that the production is carried out in the presence of an antagonist of the Mdm2 protein.

The antagonist of the Mdm2 protein is in particular used for quantitatively improving the production of the influenza virus produced, which was neither known nor suggested in the prior art.

According to one particular embodiment, the antagonist of the Mdm2 protein is an inhibitor of the interaction between the Mdm2 protein and the p53 protein.

Before describing the invention in greater detail, certain definitions of the terms used in the context of the invention will be given.

The term "influenza virus" is intended to denote all influenza viruses, and in particular human, avian, equine, porcine and feline influenza viruses. Said influenza viruses can be selected from the subtypes A, B and C. In particular, the influenza virus can be of subtype A and can in particular correspond to the H1N1, H2N2, H3N2, H4N2, H4N6, H5N1, H5N2, H7N7 and H9N2 strains, and in particular the A (H1N1) and A (H3N2) viruses. Among the H1N1 strains, mention may more particularly be made of: A/Porto Rico/8/34 (also known as A/PR/8/34), A/New Caledonia/20/99, A/Beijing/262/95, A/Johannesburg/282/96, A/Texas/36/91, A/California/969/09 A(H1N1)sov. Among the H3N2 strains, mention may more particularly be made of: A/Panama/2007/99, A/Moscow/10/99, A/Johannesburg/33/94. Among the influenza virus B subtypes, mention may, by way of examples, be made of the B/Porto Rico/8/34, B/Johannesburg/5/99, B/Vienna/1/99, B/Ann Arbor/1/86, B/Memphis/1/93, B/Harbin/7/94, N/Shandong/7/97, B/Hong Kong/330/01 and B/Yamanashi/166/98 subtypes. Although all influenza viruses, whatever their origin, are targeted by the invention, the invention is most beneficial for human influenza viruses and in particular influenza viruses circulating in the human population. According to one particular embodiment, the influenza virus is chosen from human A (H1N1) viruses and human A (H3N2) viruses. In the context of the invention, the term "virus" encompasses wild-type viruses, primary viral isolates obtained from an infected individual, recombinant viruses, attenuated viruses, reassorted viruses, and also viruses produced by reverse genetics. The "vaccine seeds" which are used for the production of vaccine are, most commonly, obtained by genetic reassortment or reverse genetics and therefore constitute a particular example of virus for the purposes of the invention.

Currently, the conventional process for producing vaccine is based, firstly, on obtaining, by genetic reassortment with the A/PR8/34 (H1N1) strain, vaccine seeds on eggs, for each of the 3 annual prototype seeds determined by the WHO for each influenza virus. Most vaccine manufacturers normally use these reassortant viruses deriving mainly from the A/PR/8/34 parental virus. Thus, each vaccine seed is the result of a process of genetic reassortment between the prototype strain and the A/PR8/34 (H1N1) virus which has replicative capacities of interest in eggs.

The viral particles of wild-type influenza viruses (also known as prototype viruses which correspond to the viruses that circulate naturally) contain eight distinct gene segments consisting of a single chain of RNA, each of the genes encoding one to three predetermined proteins of the virus: HA, NA, M1, M2, NP, NS1, NEP, PB1, PB1F2, PB1N40, PB2 and PA. The vaccine seeds obtained by reassortments correspond to a vaccine reassortant which comprises at least the segments of genes encoding HA and NA of the prototype strain on the genetic background of a prototype virus adapted for large-scale production, which currently corresponds to the A/PR/8/34 parental strain (composition "6+2"). The vaccine reassortants obtained with the 3 annual prototype strains, known as vaccine seeds, resulting from this genetic reassortment can then be amplified in eggs or in cell culture. Today, the egg system is very widely used on an industrial scale. Other techniques for producing vaccine seeds, developed over the past few years, are also based on reverse genetics. The production of vaccine seeds by reverse genetics is not, however, a registered method approved by the WHO.

Whatever the technique used for producing the vaccine seeds, the vaccines most commonly correspond to the HA and NA antigens which are purified from productions of vaccine seeds in allantoic cells or result from an in vitro cell culture. In a vaccine, these glycoproteins can optionally be combined with adjuvants. Currently, the vaccine doses are defined by a fixed amount of HA antigen (15 micrograms/viral subtype/dose). Positive detection of the NA antigen is necessary for the validation of the vaccine batches.

In the context of the invention, the term "Mdm2 antagonist" is intended to mean a molecule capable of interacting with Mdm2 and of blocking, at least partly, its biological activity. In particular, in the context of the invention, the Mdm2 antagonist used will behave like an inhibitor of the interaction between the Mdm2 protein and the p53 protein.

An "inhibitor of the interaction between the Mdm2 protein and the p53 protein" can be defined as a compound which prevents the interaction between the p53 and Mdm2 proteins. Such compounds, which are, for example, Mdm2-targeting antisense deoxynucleotides, or more broadly developed, peptide or nonpeptide low-molecular-weight molecules, bind to the interface between p53 and Mdm2 and prevent the association thereof.

The p53 tumor suppressor protein plays a central role in regulation of the cell cycle, apoptosis, DNA repair and numerous metabolic pathways. By virtue of its central position, p53 is the protein most commonly mutated in tumors in human beings. Indeed, close to 50% of cancers exhibit mutations of the p53 gene, resulting in inactivation or loss of the protein. More broadly, p53 functions are most of the time inhibited in cancers. Under normal conditions, the activity and the amount of p53 are closely regulated by the Mdm2 protein (Murine double minute 2, or also known as Hdm2). This ubiquitous protein is an E3 ubiquitin ligase which is, inter alia, capable of interacting directly with p53, the formation of the complex between the two proteins constituting a step of an autoregulatory loop: when p53 is activated, it binds to the P2 promoter of Mdm2 and induces the transcription and expression of Mdm2. In return, Mdm2 is, for its part, capable of binding to p53 and of inhibiting it by various mechanisms (p53 transactivating activity inhibition, delocalization of p53 out of the nucleus and degradation of p53 via the proteasome) (Freedman et al. Cell Mol Life Sci. 1999 January 55(1), 96-107).

Any Mdm2 antagonist, and in particular any inhibitor of the interaction between Mdm2 and p53, can be used in the context of the invention. The most well known properties of these compounds are the induction of the activity of the p53 protein, but also the inhibition of cell proliferation. The interaction between the p53 and Mdm2 proteins involves the amino-terminal regions of the two partners. These regions of interaction have been determined by double hybrid (yeast) methods, but also by immuno-precipitation experiments. They correspond, on p53, to region 1 to 41/52 and, on Mdm2, to region 1/19 to 118/202. Site-directed mutagenesis experiments have shown several residues on p53 which are important in the interaction with Mdm2: Leu14, Phe19, Leu22 and Trp23 (Klein C, et al. Br. J. Cancer. 2004 Oct. 18; 91(8):1415-9).

The principal method for evaluating the effectiveness of compounds inhibiting the interaction between the p53 and Mdm2 proteins consists in calculating a 50% inhibitory concentration (IC50) and indirectly an inhibition constant (Ki, via the Cheng-Prusoff equation), by producing a curve of response, as a function of the biological parameter that it is sought to inhibit, namely the p53/Mdm2 interaction.

For example, it is possible to calculate the IC50s by surface plasmon resonance (SPR, Biocore) measurement, by bringing the inhibitory molecule into competition with Mdm2: various concentrations of compounds are incubated with recombinant Mdm2 protein and injected into a chamber (SPR) with a chip onto which the recombinant p53 protein is grafted, as described by Vassilev et al., in Science. 2004 Feb. 6; 303(5659):844-8. Other tests based on fluorescence measurement techniques can also be used (Kane et al. Anal Biochem. 2000 Feb. 1; 278(1):29-38, Lu et al. J Med. Chem. 2006 Jun. 29; 49(13):3759-62). In the case of the family of molecules such as Nutlin-3, the compounds have an IC50 of approximately 100-300 nm (Vassilev et al, 2004, above). In the case of the NSC66811 molecule, the Ki constant is 120 nM (Lu et al 2006, above).

In such competition experiments, it is possible to introduce, as a control, a natural peptide derived from p53, and in particular the peptide corresponding to residues 13 to 29 of p53 and of SEQ ID No 1: PLSQETFSDLWKLLPEN-NH2 as described by Lu et al., 2006, above, of which the Ki constant measured and given in this publication is 6670 nM. Compounds which exhibit a Ki or an IC50 lower than that of this peptide, on at least one of the competition tests described in Vassilev et al., 2004, Kane et al., 2000 and Lu et al, 2006, above, are in particular considered to be inhibitors of the Mdm2/p53 interaction in the context of the invention. More generally, a compound which exhibits, in the competition test described in Lu et al., 2006, above, and in the supporting information JM060023, a Ki of less than 10 μM, preferably less than 5 μM and even more preferentially less than 1 μM, will be preferred.

By way of examples of an "inhibitor of the interaction between the Mdm2 protein and the p53 protein" that can be used in the context of the invention, mention may be made of imidazoline derivatives (and in particular those described in U.S. Pat. No. 6,734,302, WO 03/051359, WO 2007/082805, WO 2007/063013, EP 1463501, WO 2006/097261, US 2008/0255119 and WO 2008/130614), imidazole derivatives (and in particular those described in WO 2008/130614 and WO 2008/119741), oxindole derivatives (and in particular those described in U.S. Pat. No. 7,576,082 and WO 2008/034736), spiroindolinone derivatives (and in particular those described in EP 1856123, 1 Med. Chem. 2006, 49, 3432-5, U.S. 60/781, 958, U.S. Pat. No. 7,495,007, WO 2007/104714 and WO 2008/141975), quinoline derivatives, and in particular isoquinolinederivatives (and in particular those described in WO 2008/034039, US2009/0068144 and ChemMedChem 2008, 3, 1118-28), bisarylsulfonamide derivatives (and in particular those described in EP 1519932), benzodiazepine derivatives (and in particular those described in J. Med. Chem. 2005, 48, 909-12, EP 1443937 and U.S. Pat. No. 7,115,598), piperidine derivatives (and in particular those described in U.S. Pat. No. 7,060,713 and WO 2008/005268), phenoxyacetic acid derivatives or phenoxymethyltetrazole derivatives (and in particular those described in EP 0947494), chalcone derivatives (and in particular those described in Biochemistry, 2001, 40, 336-44 and U.S. Pat. No. 7,514,579), tetrazole derivatives (and in particular those described in US 2008/0262200), disulfide derivatives (and in particular those described in US 2009/008553), diaminoaryl derivatives (and in particular those described in WO 2006/032631, WO 2007/107543 and WO 2007/107545) or else peptide derivatives (and in particular those described by Bottger et al., in Research Paper, 7(11), 1997, 860-9), described as inhibitors of the Mdm2 protein in the prior art. A review of such inhibitors is given in the publications by Lutz Weber in Expert Opin. Ther. Patents 2010, 20(2), 179-190 and by Shangary et al., in Annu Rev PharmacolToxicol. 2009; 49:223-41, to which reference may be made for further details.

By way of more precise examples, mention may be made of:

Nutlin-3, (±)-4-[4,5-bis(4-chlorophenyl)-2-(2-isopropoxy-4-methoxy-phenyl)-4,5-dihydroimidazole-1-carbonyl]piperazin-2-one, described by Vassilev et al., Science. 2004 Feb. 6, 303(5659), 844-8, of formula:

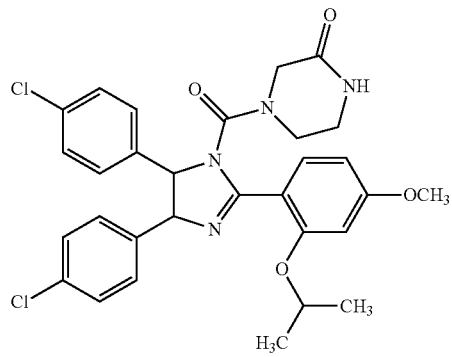 [SMILES: COc1ccc(C2=NC(c3ccc(Cl)cc3)C(c3ccc(Cl)cc3)N2C(=O)N2CCNC(=O)C2)c(OC(C)C)c1]

which is the subject of two phase I clinical trials in oncology, the NSC66811 molecule (2-methyl-7-[phenyl(phenylamino)methyl]-8-quinolinol) of formula:

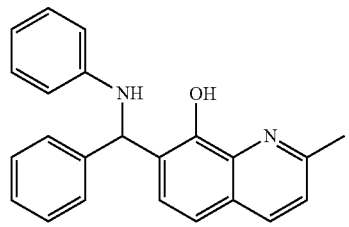 [SMILES: Cc1ccc2ccc(C(Nc3ccccc3)c3ccccc3)c(O)c2n1]

and the molecules having the following formula:

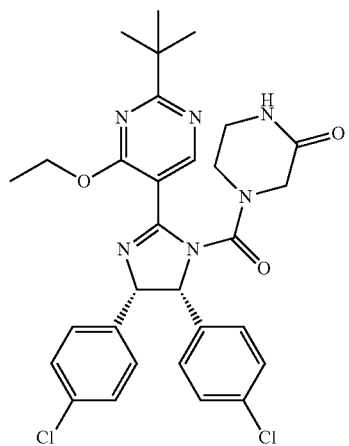

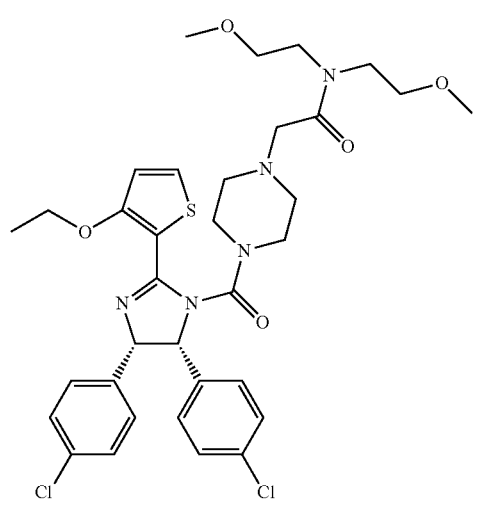

-continued
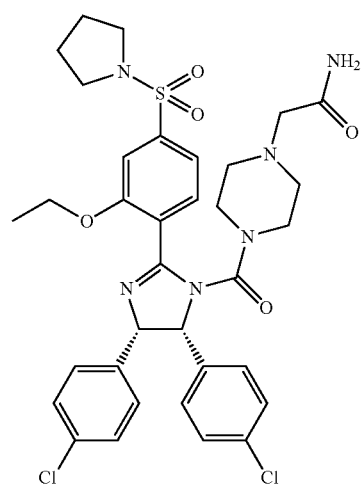
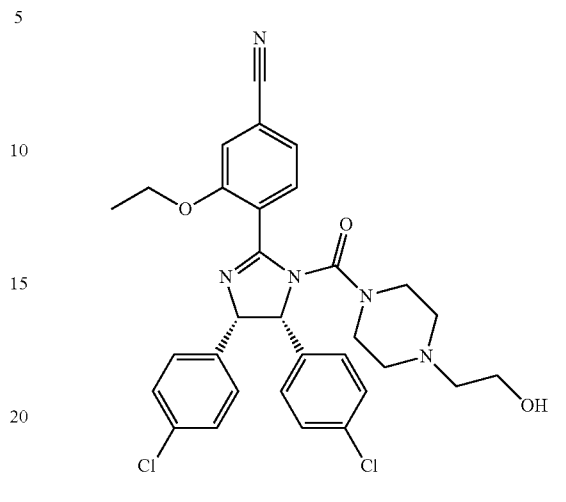
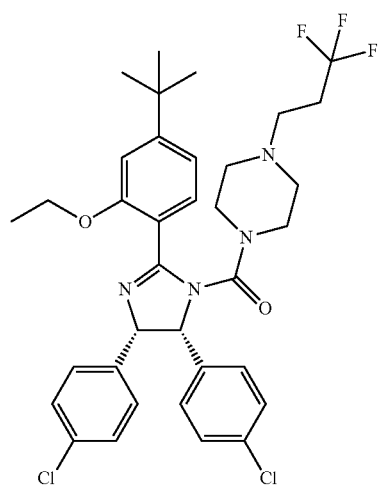
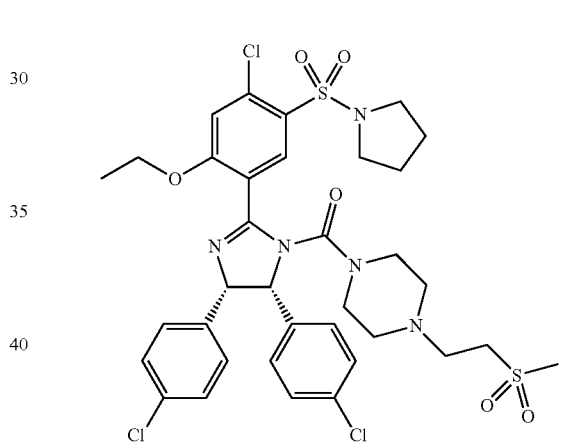
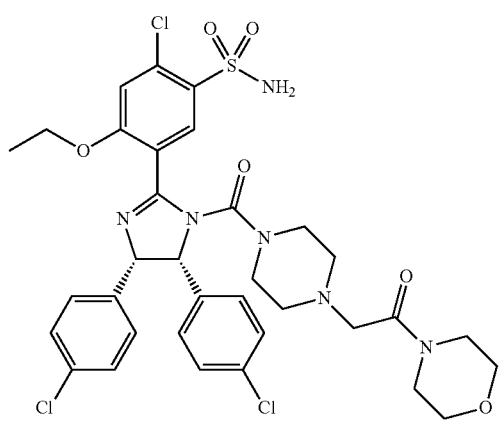
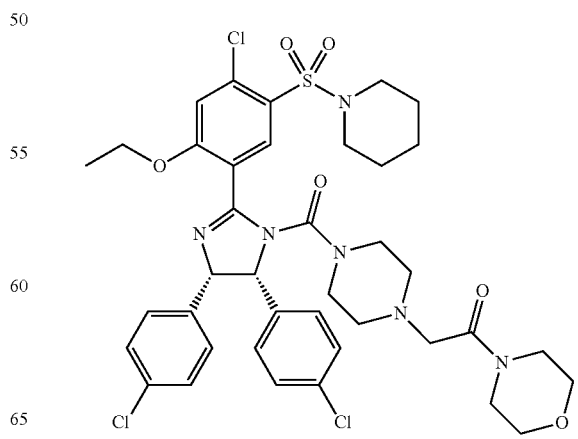

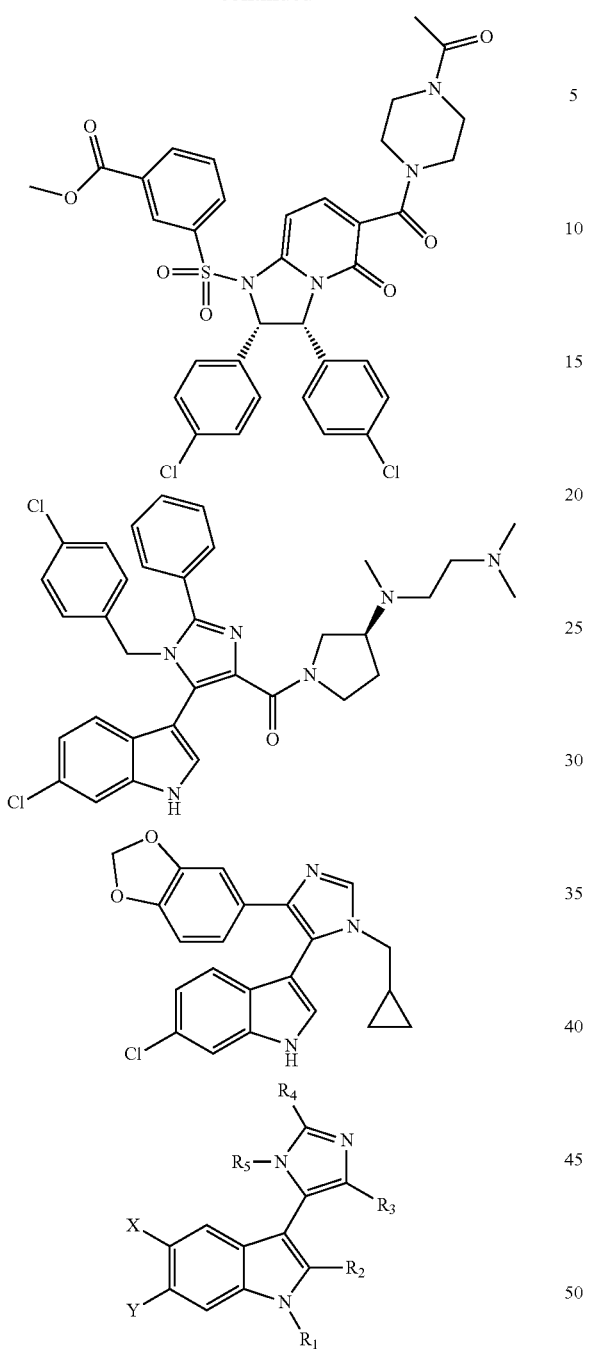
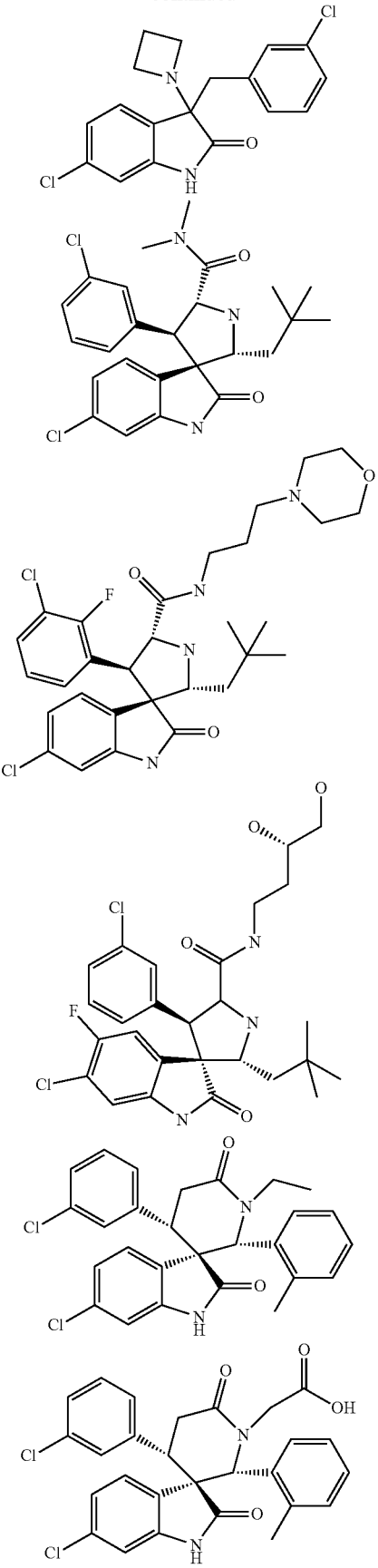
with X, Y, $R_1$, $R_2$, $R_3$, $R_4$ and $R_5$ as described in patent application WO 2008/119741

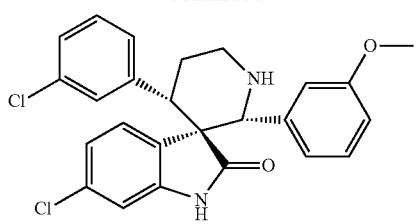
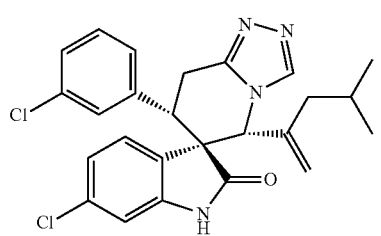
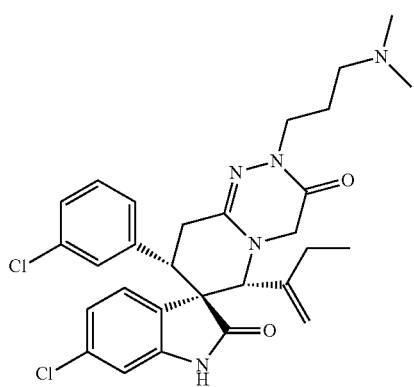
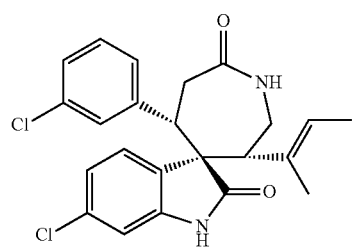
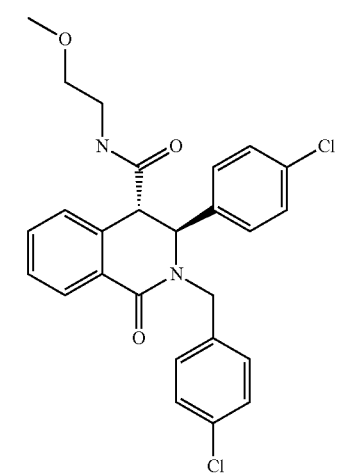
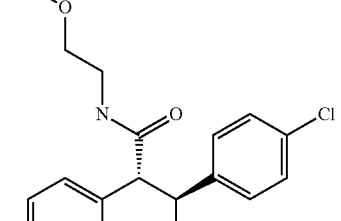
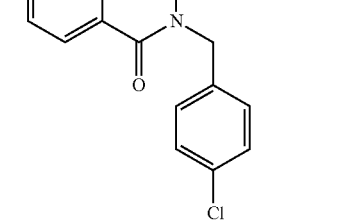
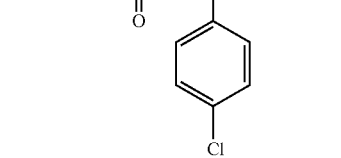

Such molecules are known for their use in the treatment of cancer, but their use for quantitatively improving influenza virus production has never been envisioned. The contribution of the invention lies in the use of an Mdm2 antagonist, and preferably of an inhibitor of the interaction between the Mdm2 protein and the p53 protein, for the production of influenza viruses or vaccine seeds. Any techniques known for the production thereof can be used.

The production of influenza viruses or vaccine seeds is carried out in a cell system, in the presence of an Mdm2 antagonist, and in particular of an inhibitor of the interaction between the Mdm2 protein and the p53 protein.

Several parameters that will be adjusted by those skilled in the art can have an influence on the effect of the Mdm2 antagonist, and in particular of the inhibitor of the interaction between the Mdm2 protein and the p53 protein: amount of inhibitor, moment at which the inhibitor is added, initial amount of virus at the time of the infection, production time.

For example, the Mdm2 antagonist, and in particular the inhibitor of the interaction between the Mdm2 protein and the p53 protein, will be used at a concentration of from 0.1 to 100 µM. In particular, when an imidazole derivative, such as Nutlin-3, is used, a concentration of from about 1 µM to 10 µM will preferably be chosen, and when a quinoline derivative, such as NSC66811, is used, a concentration of from about 0.5 µM to 5 µM will preferably be chosen.

The cell system selected (egg or cell culture) is infected with an influenza virus or an influenza vaccine seed. The addition of the Mdm2 antagonist, and in particular of the inhibitor of the interaction between the Mdm2 protein and the p53 protein, can be carried out before, after or at the same time as the infection. The production of the viruses, and in particular the vaccine seeds, can in particular be carried out in allantoic cells in an embryonated chicken egg or else in vitro in cell culture. The cells used can be any type of cells suitable for the cell culture, replication and production of viruses and the production of viral antigens. Advantageously, the cells are chosen from mammalian cells of human or animal origin, avian cells or insect cells.

Among the mammalian cells, mention will in particular be made of culture cells derived from human cells, from porcine cells or from dog cells. These cells can in particular be derived from lung epithelial cells (for example: human lung carcinoma A549 CCL-185) or intestinal epithelial cells (Caco-2 ATCC HTB-37).

Among the mammalian cells, mention will also be made of the following cells:
SJPL porcine lung epithelial cells, including in particular the PTA-3256 line deposited at the ATCC (US2004/0142450 and WO2009/059411),
MDCK cells from dog,
BHK21 CCL-10 *Mesocricetus auratus* (hamster), HOS human cells, including in particular the CRL-1543 line.

In one particular embodiment, the cells are avian cells adapted to cell culture, such as, for example:
CCL-141 *Anasplatyrhynchus domesticus,*
CRL-12135 *Gallus gallus* Con A-C1-VICK,
CRL-12203. *Gallus gallus* UMNSAH/DF-1,
CRL-12357 *Gallus gallus* ConA-B1-VICK,
CRL-1590 *Gallus gallus* SL-29,
CRL-1708 *Coturnixcoturnix japonica* QT6,
CRL-1962 *Coturnixcoturnix japonica* QM7 (Quail muscle clone 7),
CRL-2111 *Gallus gallus* (chicken) DT40,
CRL-2112 *Gallus gallus* (chicken) DT95,
CCL-8135 *Meleagris gallopavo* (turkey) MDTC-RP19, and
the QM7 myoblast line deposited at the ATCC(CRL-1632), described in document US2005/0084503.

Other avian cell lines are known to those skilled in the art and can be used. They may in particular be avian embryonic cells. The EB66 and EBx cell lines have been described in WO03/076601 and WO2008/129058. Lohr et al. describe the establishment of AGE1.CR and AGE1.CR.pIX avian cell lines for viral propagation or replication. WO 2009/004016 also describes immortalized avian cells for viral production and the methods for preparing them.

According to one particular embodiment, these cells are chosen from MDCK, Vero and A549 cells and generally from the avian cell lines used for influenza virus production.

MDCK cells are, for example, described in US2006/0188977 and EP1862537. The following lines will in particular be mentioned: MDCK-SF101 (ATCC PTA-6501), MDCK-SF102 (ATCC PTA-6502) and MDCK-SF103 (ATCC PTA-6503).

The cells are, for example, chosen from the following cells:
Vero cells, in particular the CCL-81 *Cercopithecus aethiops* Vero line;
CHO cells, in particular the CRL-12444 *Cricetulus griseus* (Chinese hamster) and CHO DP-12 clone #1933 aIL8.92 NB 28605/12 lines;
MDCK cells, in particular the CCL-34 *Canis familiaris* MDCK (NBL-2) line,
COS cells, in particular the CRL-1650 *Cercopithecus aethiops,* COS-1 CRL-1651 *Cercopithecus aethiops* and COS-7 lines;
CV1 cells, in particular the CCL-70 *Cercopithecus aethiops* CV-1 lines,
HeLa cells, and
Hep-2 cells.

The use of CV-1, CV-C, Vero and BSC-1 cell lines for viral production is, for example, described in U.S. Pat. No. 6,303,371.

In advantageous embodiments, the cells are chosen from CHO, MDCK, COS, CV-1, Vero, BHK21, PERC6, A549, HEK, HeLa, AGE1.CR, AGE1.CR.pIX, EB66, EBxand Hep-2. Advantageously, the cells are chosen from cell lines which have regulatory authorizations for the viral production in cell culture for medical purposes.

According to one particular embodiment, the method for producing influenza viruses according to the invention comprises the following steps: a) infection with an influenza virus, and in particular with influenza vaccine seeds, of a cell system which can either be an embryonated chicken egg, or cells of a cell line in a cell culture medium; b) incubation of the production cell system selected and infected in step a), under conditions which allow the replication of said influenza virus, and in particular of the influenza vaccine seeds; c) harvesting of the whole influenza virus, and in particular of the vaccine seeds, produced in particular in the culture supernatant and/or in said cells in culture. In the case of an egg system, the culturing is carried out in vivo, whereas in the case of a cell line, it is carried out in vitro.

The use of an Mdm2 antagonist, and in particular of an inhibitor of the interaction between the Mdm2 protein and the p53 protein, can be implemented in the production of any type of influenza virus, in particular of a wild-type virus, of a primary viral isolate obtained from an infected individual, of a recombinant virus, of an attenuated virus, of a reassorted virus, or of a virus produced by reverse genetics.

According to one particular embodiment, the production can be carried out in a cell system, in vitro. The infection of the cells of a cell line with the selected influenza virus is carried out in a cell culture medium which is preferably a serum-free medium, and even more preferably a medium free of proteins of animal origin (calibrated synthetic medium). According to one particular embodiment, the culturing of the infected cells is carried out in the presence of a proteolytic enzyme in the culture medium, under conditions sufficient to ensure propagation of the virus in the culture. Said proteolytic enzyme is, for example, selected from trypsin, chymotrypsin, thermolysin, pepsin, pancreatin, papain, pronase, subtilisin A, elastase, furin and carboxy-peptidase. Advantageously, this enzyme is a recombinant enzyme and is therefore not of animal origin.

The method according to the invention can be applied to the production of reassortant influenza viruses, owing to the fragmented nature of influenza viruses. In this case, the cell system selected is infected with at least two influenza virus strains, which results in the production of a mixture of segments derived from the two strains of virus in a single host cell. During the assembly of the viruses, all the combinations of fragments are theoretically possible. The new combinations are called reassortants. Particular reassortants can be selected by suppression or elimination of the other viruses, for example by means of antibodies. The vaccine seeds are generated according to this type of method. For further details on these techniques, reference may be made to Kilnourne E. D. in Plotkin S A and Mortimer E. A. Eds, Vaccines 1994.

The method according to the invention can also be applied to the production of influenza viruses by reverse genetics. In particular, expression plasmids can be transfected into the cells and thus allow the production of recombinant virus (J Gen Virol. 2000 December; 81(Pt 12):2843-7). Another, less widely used, technique consists in using modified transcripts of the viral RNAs of the influenza virus which are transcribed in vitro from a cDNA construct in the presence of purified proteins, in particular purified NP, PB1, PB2 and PA proteins. The synthetic ribonucleo particles thus produced are then transfected into cells previously infected with an influenza virus. For further details on the latter technique, reference may be made to Enami, Proc. Natl. Acad. Sci. 8th, 1990, 3802-3805, to Enami and Palese, 1 Virol. 1991, 65, 2511-2513 (1991) and to Luytjes, Cell. 1989, 59, 1107-1113.

In the context of the invention, according to one particular embodiment, the method for preparing an influenza virus, and in particular a vaccine seed, according to the invention can comprise a step of inactivating the virus harvested. The inactivation can be carried out according to any known technique, and, for example, by virtue of a treatment with formaldehyde, beta-propiolactone, ether, ether with a detergent (such as Tween-80), cetyltrimethylammonium bromide (CTAB), Triton N102, sodium deoxycholate or tri-N-butyl phosphate.

The method for producing viruses and in particular vaccine seed according to the invention can be included in a method for manufacturing vaccine. In this case, the method for preparing a vaccine according to the invention comprises a step of producing antigenic surface proteins (HA and NA) from a whole influenza virus produced. In this case, it may be necessary to treat the medium, in particular the supernatant, containing the whole virus obtained, with an enzyme for digesting deoxyribonucleic acids (DNA), for example DNase or nuclease enzymes. It is also possible to add a cationic detergent, such as a cetyltrimethylammonium or myristyltrimethylammonium salt, lipofectin or lipofectamine.

The harvesting of the virus or of the surface proteins is most commonly accompanied by concentration and/or purification and is carried out according to techniques well known to those skilled in the art, using in particular ultrafiltration or centrifugation (as described, for example, in Furminger, in Nicholson, Webster and Hay (Eds.), Textbook of influenza, chapter 24 pp 324-332).

The vaccine obtained by virtue of the method according to the invention can correspond to killed (also referred to as inactivated) pathogens or to live attenuated pathogens. The vaccine can, for example, correspond to the culture supernatant obtained after the production of virus or else to the antigenic surface proteins that can be obtained using the virus produced in accordance with the method according to the invention.

The examples hereinafter, with reference to the appended figures, make it possible to illustrate the invention but are in no way limiting in nature.

For all the following examples, the experiments were carried out at a temperature of 37° C. The culture medium used is DMEM (Ref 41966, Gibco), supplemented with trypsin (1 ug/mL, Sigma) during the infections.

1) EFFECT OF NUTLIN-3 ON THE CYTOPATHIC EFFECTS INDUCED BY INFLUENZA

Test Carried Out on A549 Cells with the H3N2 A/Moscow/10/99 Virus

A549 cells (ATCC, American Type Culture Collection CCL185) are cells derived from a lung carcinoma. They exhibit similar characteristics (polarized epithelial cells derived from the human respiratory tract) to type II alveolar epithelial cells (Lieber et al. Int J. Cancer. 1976 Jan. 15; 17(1):62-70). Several ex-vivo studies on lung tissues from infected patients have shown that epithelial cells of this type probably constitute the primary influenza virus infection site (Nicholls et al. Nat. Med. 2007 February; 13(2):147-9, van Riel et al. Science. 2006 Apr. 21; 312(5772):399). These cells are therefore considered to be relevant for studying influenza viruses and are, consequently, very widely used in the field of fundamental research on influenza viruses.

Figure 1:
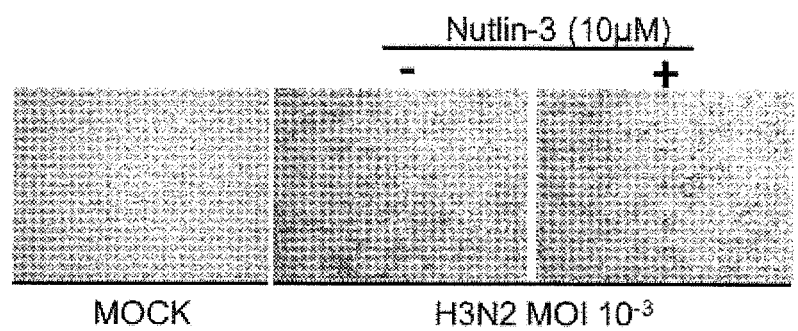
FIG. 1 shows photographs of an uninfected A549 cell layer and of an A549 cell layer infected with the H3N2 virus, in the presence or absence of Nutlin-3.

The observation and monitoring of the cytopathic effects induced by the virus over time generally allow a first evaluation of the degree of infection of the cell layer. The cytopathic effect induced by the virus is characterized in particular by fusion of the infected cells with one another, forming multinucleated cell structures (syncytia). By photon microscopy, observation of the amount and of the scale of these structures on the cell layer makes it possible to obtain an estimation of the degree of infection. Comparison of the cytopathic effects obtained in the presence or absence of Nutlin-3 (10 μM), under the same infection conditions (MOI (multiplicity of infection)=$2 \times 10^{-3}$), revealed considerable differences, that could be observed from 24 hpi (hours postinfection) onward, as demonstrated in FIG. 1 with, as reference, the uninfected (MOCK) cells. In the absence of Nutlin-3, the A549 cells exhibit a cytopathic effect characteristic of an advanced infection, with numerous cell aggregates and numerous syncytial structures. In comparison, the cells treated with Nutlin-3 (molecule added 14 h before the infection and then retained during the infection) exhibit a more marked cytopathic effect, with in particular the presence of much greater syncytial infection structures.

2) EFFECT OF NUTLIN-3 ON VIRAL PRODUCTION

Test Carried Out on A549 Cells with the H3N2 A/Moscow/10/99 Virus

Figure 2:
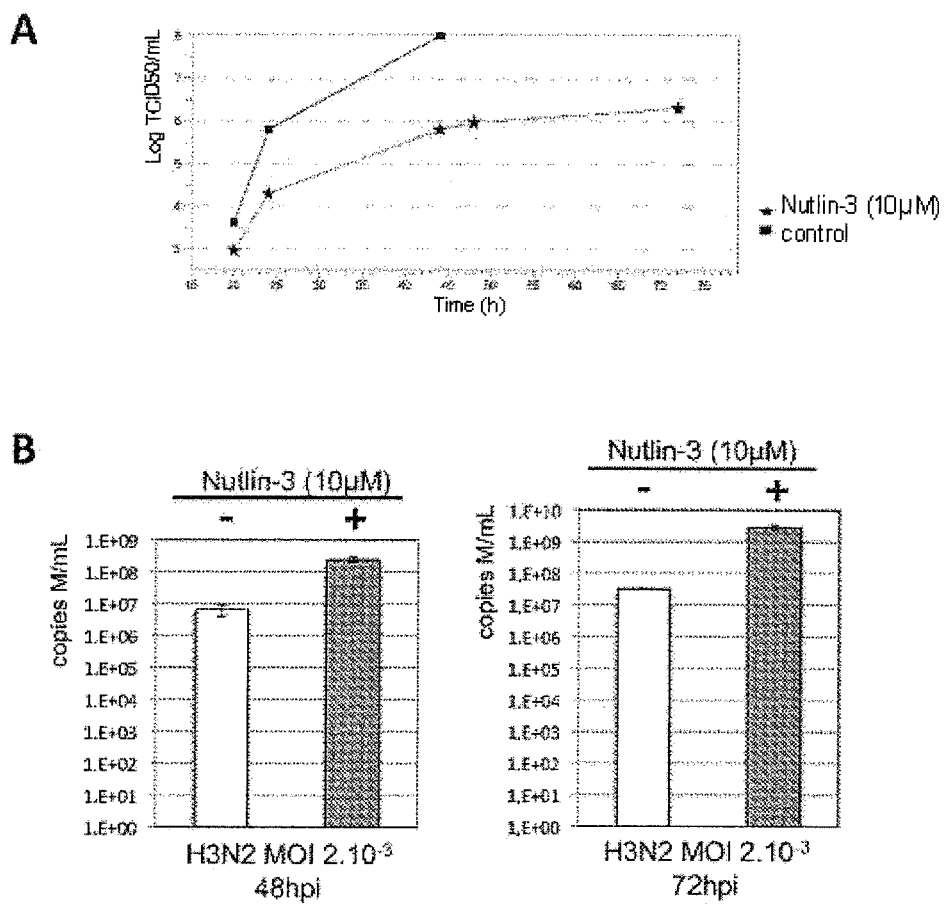

The quantification of the viruses produced and released during the infection, by determining the infectious titer (TCID50/ml) in the supernatant over time, indicates a much greater amount of viral progeny in the presence of Nutlin-3 (gain of one log 10 difference from 24 hpi onward, FIG. 2A). In order to gain a more precise idea, the quantification of the number of copies of viral genome M/ml of supernatant was then carried out, by extraction of the viral RNAs and quantification by real-time RT-qPCR (FIG. 2B). At 48 hpi, $6.66 \times 10^6$ copies M/ml were measured in the absence of Nutlin-3, compared with $2.44 \times 10^8$ copies M/ml in the presence of Nutlin-3, i.e. a gain of more than 36-fold in terms of viral production. The same calculation performed at 72 hpi indicates a gain of 88-fold in favor of the conditions where Nutlin-3 is used.

3) EFFECT OF NUTLIN-3 ON THE TITERS OF VIRUSES PRODUCED AFTER ONE OR MORE CYCLES OF VIRAL REPLICATION, USING VARIOUS INITIAL AMOUNTS OF INOCULATED VIRUSES

Evaluation of the Effect of a Pretreatment and of the Various Concentrations of Nutlin-3 a) Test Carried Out on A549 Cells with the H3N2 A/Moscow/10/99 Virus

Figure 3:
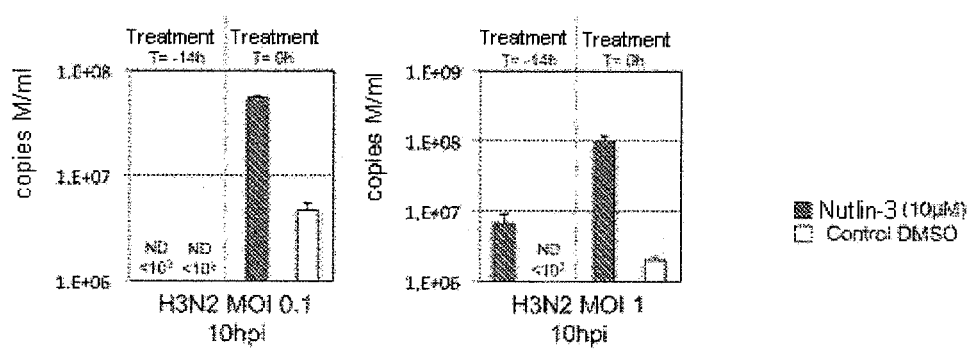
FIGS. 2 to 7 show the observed amounts of copies of viral genome M/ml in the culture supernatant (M for the segment of viral genome encoding the M1 and M2 viral proteins), with various culture conditions and after various infection times.

The A549 cells were infected with various amounts of virus (MOI 0.01, 0.1 and 1), in the presence or absence of Nutlin-3, and the amount of copies M/ml of supernatant was measured by RT-qPCR after a single viral cycle (10 hpi) or after several viral cycles (28 hpi). The cells were brought into contact with Nutlin-3, either 14 h before the infection (T=−14 h), or immediately at the time of infection (T=0 h) (FIG. 3). In any event, the Nutlin-3 is added in one go.

On the timescale of a single viral cycle (10 hpi), the viral genome in the supernatant could be quantified only under the infection conditions with MOIs of 0.1 and 1. Higher amounts of copies M/ml of supernatant are observed when the cells are in the presence of Nutlin-3. For example, when the treatment is started at T=0, in the presence of Nutlin-3, 11 to 50 times more copies of genome are measured in the supernatant of infected cells than the control without Nutlin-3, respectively for MOIs of 0.1 and of 1 (FIG. 3).

Figure 4:
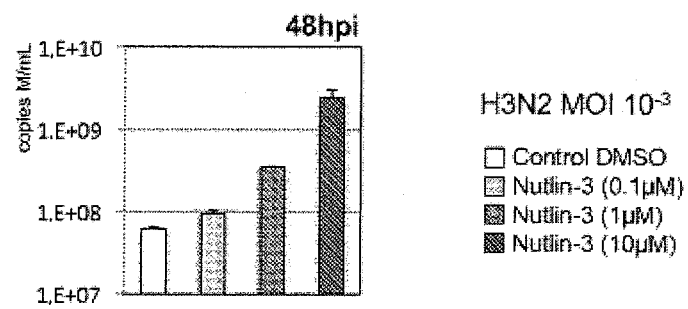

A similar experiment was carried out with an MOI of $10^{-3}$, while modifying the time at which the pretreatment is carried out (14 h compared with 10 h before infection). At 48 hpi, Nutlin-3 makes it possible to obtain 1.5, 5.7 and 40 times more copies M/ml of supernatant than the control for respective concentrations of 0.1, 1 and 10 µM (FIG. 4).

b) Test Carried Out on MDCK Cells with the H3N2 A/Moscow/10/99 Virus

The MDCK line (ATCC No. CCL-34) is the most widely used line for the laboratory production of influenza virus. It is a cell line which is also registered and with which batches of vaccine have been produced by Novartis and Solvay.

Figure 5:
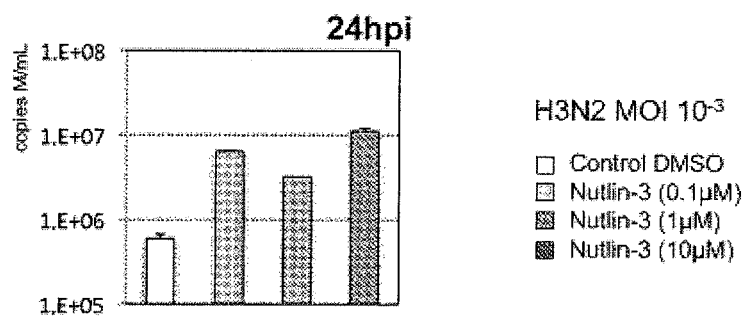

The results shown in FIG. 5 indicate that, at an initial MOI of $10^{-3}$, the Nutlin-3 molecule at various concentrations (0.1, 1 and 10 µM), with a pretreatment 14 h before the infection, greatly increases the viral titer (copies of genome M/ml) in the cell supernatants after several consecutive viral cycles. At 24 hpi, up to 19 times more copies of genome M/ml are obtained in the presence of Nutlin-3 compared with the control. These additional data confirm the results obtained with the A549 cell line.

4) EFFECT OF ANOTHER MDM2 ANTAGONIST MOLECULE (NSC66811) ON VIRAL REPLICATION

Test Carried Out on A549 Cells with the H3N2 A/Moscow/10/99 Virus

The NSC66811 molecule (2-methyl-7-[phenyl(phenylamino)methyl]-8-quinolinol, Merck Biosciences) of formula:

is known to interact with Mdm2 and thus also to block the p53/Mdm2 interaction (effect similar to that of Nutlin-3).

This molecule was used at concentrations of 2 and 20 µM with an MOI of $10^{-3}$.

Figure 6:
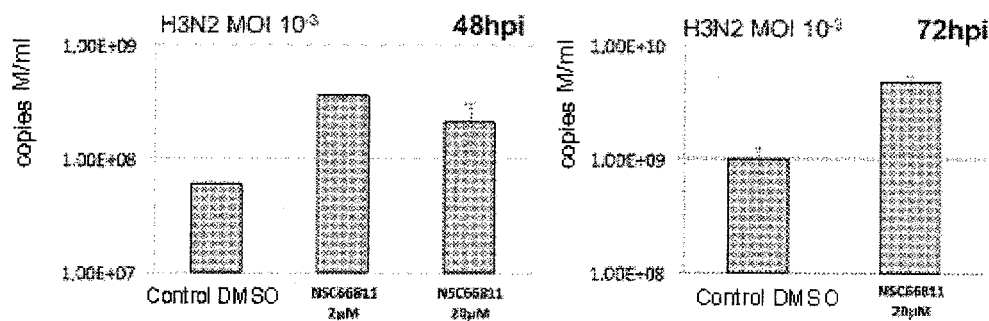

The results obtained at 48 hpi are given in FIG. 6 and show that the NSC66811 molecule makes it possible to obtain results that are entirely similar to those previously described for the Nutlin-3 molecule. Thus, at 48 hpi, an NSC66811 concentration of 2 µM makes it possible to obtain approximately 6 times more copies of genome M in the supernatant compared with the control. Similarly, at 72 hpi, an NSC66811 concentration of 20 µM makes it possible to obtain approximately 5 times more copies of genome M in the supernatant compared with the control.

5) EFFECT OF THE OVEREXPRESSION OF MDM2 ON VIRAL REPLICATION

Test Carried Out on A549 Cells with the H3N2 A/Moscow/10/99 Virus

Figure 7:
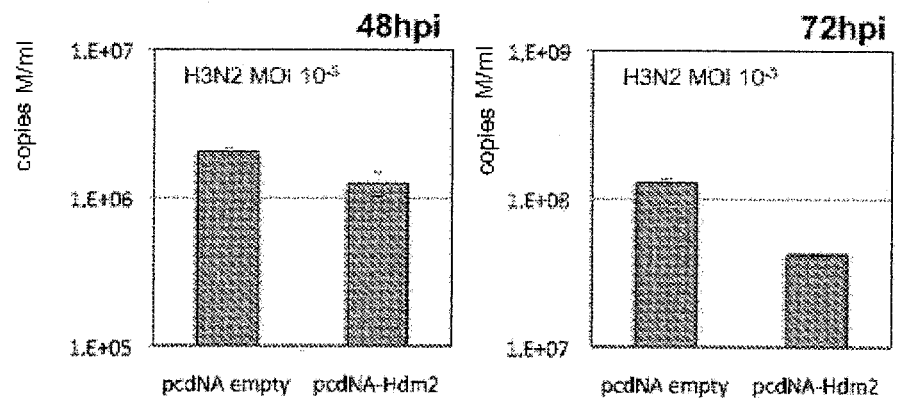

The effect of the overexpression of Mdm2 on viral production was also studied. The results shown in FIG. 7 which give the number of copies at 48 hpi and 72 hpi, with an initial MOI of $10^{-3}$, show that the H3N2 virus replicates less efficiently when the Mdm2 protein is overexpressed (pcdNA-Hdm2). This result confirms that the effect of the molecules tested on the production of influenza viruses is indeed linked to their antagonist action on the Mdm2 protein.

6) CONCLUSIONS

All the experiments presented in 1), 2), 3), 4) and 5) show a clear effect of Nutlin-3 or of another Mdm2 antagonist molecule (NSC66811) on the viral production of influenza viruses, on two different cell systems (A549/MDCK). The functional link between the mode of action of the two molecules tested (inhibitor of the p53-Mdm2 interaction) and their modulating properties on the cell production of influenza viruses is supported by the results obtained under the conditions of Mdm2 overexpression.

The invention claimed is:

1. A method for producing an influenza virus comprising: a) infecting a cell system that excludes human beings with an influenza virus; b) adding an Mdm2 antagonist to the cell system before, after, or at the same time as said infecting, c) incubating in the presence of the Mdm2 antagonist the cell system selected and infected in step a) under conditions which allow replication of said influenza virus; and d) harvesting of the whole influenza virus produced.

2. The method for producing an influenza virus as claimed in claim 1, characterized in that the Mdm2 antagonist is used for quantitatively improving the production of the influenza virus produced.

3. The method for producing an influenza virus as claimed in claim 1, characterized in that the Mdm2 antagonist is an inhibitor of the interaction between the Mdm2 protein and the p53 protein.

4. The method for producing an influenza virus as claimed in claim 1, characterized in that the influenza virus is chosen from the subtypes A, B and C.

5. The method for producing an influenza virus as claimed in claim 1, characterized in that the influenza virus is a vaccine seed.

6. The method for producing an influenza virus as claimed in claim 1, characterized in that the production is carried out in allantoic cells in an embryonated chicken egg.

7. The production method as claimed in claim 1, characterized in that the production is carried out in vitro in cell culture.

8. The method for producing an influenza virus as claimed in claim 7, characterized in that the production is carried out in vitro in a cell line chosen from CHO, MDCK, COS, CV-1, Vero, BHK21, PERC6, A549, HEK, HeLa, AGE1.CR, AGE1.CR.pIX, EB66, EBx, and Hep-2 lines.

9. The method for producing an influenza virus as claimed in claim 1, characterized in that the virus is a wild-type virus, a primary viral isolate obtained from an infected individual, a recombinant virus, an attenuated virus, a reassorted virus, or a virus produced by reverse genetics.

10. The production method as claimed in claim 1, characterized in that the Mdm2 antagonist is an inhibitor of the interaction between the Mdm2 protein and the p53 protein, chosen from imidazoline derivatives, imidazole derivatives, oxindole derivatives, spiroindolinone derivatives, quinolone, bisarylsulfonamide derivatives, benzodiazepine derivatives, piperidine derivatives, phenoxyacetic acid derivatives, phenoxymethyltetrazole derivatives, chalcone derivatives, tetrazole derivatives, disulfide derivatives, diaminoaryl derivatives and peptide derivatives.

11. The method as claimed in claim 1, characterized in that the Mdm2 antagonist is an inhibitor of the interaction between the Mdm2 protein and the p53 protein, chosen from:

Nutlin-3, (±)-4-[4,5-bis(4-chlorophenyl)-2-(2-isopropoxy-4-methoxyphenyl)-4,5-dihydroimidazole-1-carbonyl]piperazin-2-one of formula:
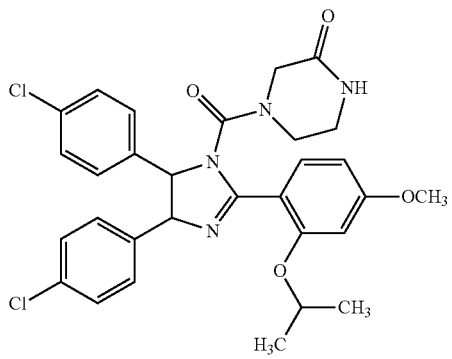
the NSC66811 molecule (2-methyl-7-[phenyl(phenylamino)methyl]-8-quinolinol) of formula:
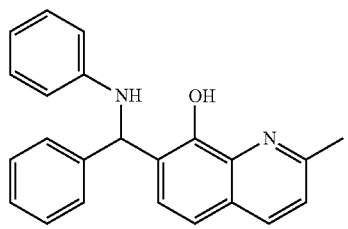 [SMILES: Cc1ccc2ccc(C(Nc3ccccc3)c3ccccc3)c(O)c2n1]
and the molecules having the following formula:
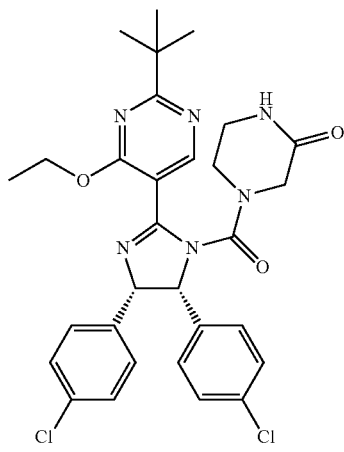
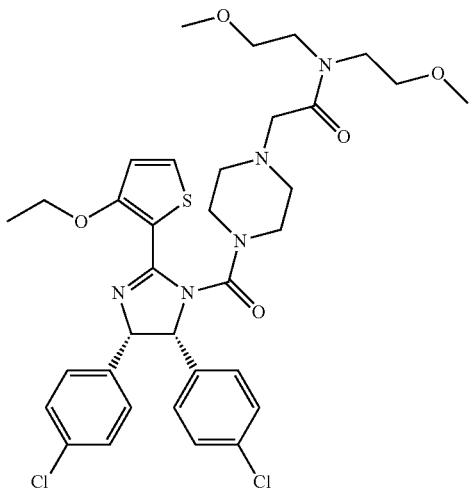
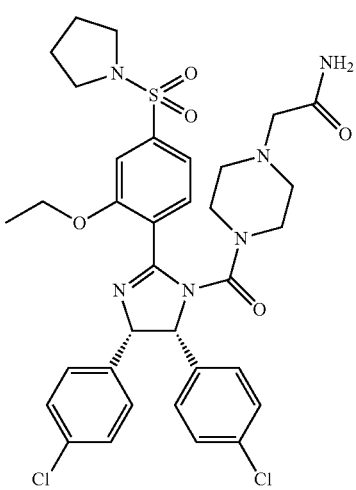
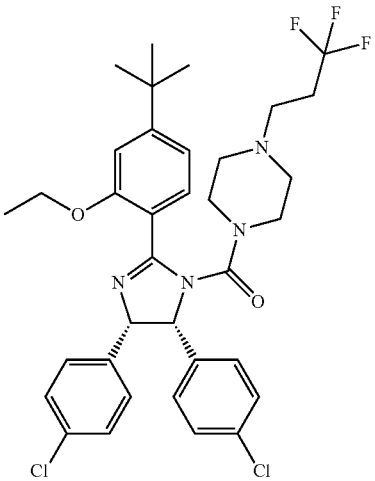

23
-continued
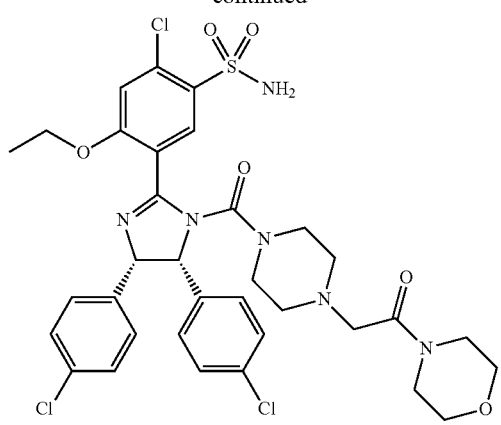
24
-continued
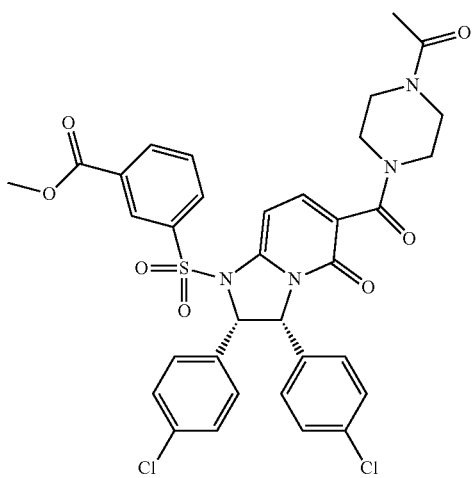
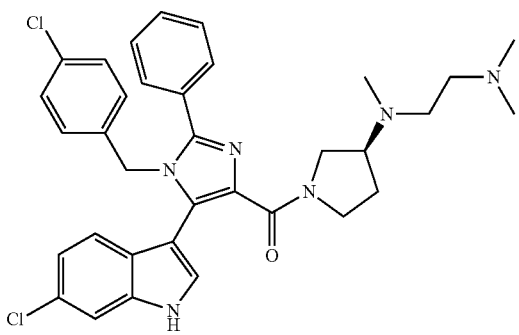
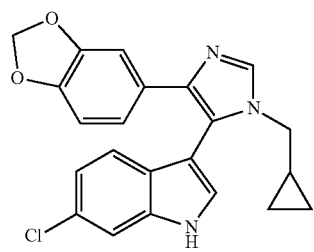
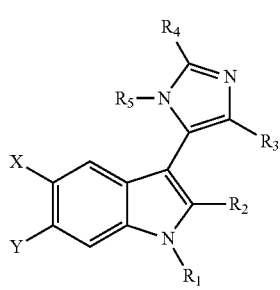
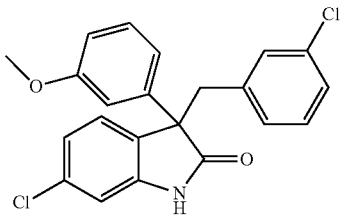

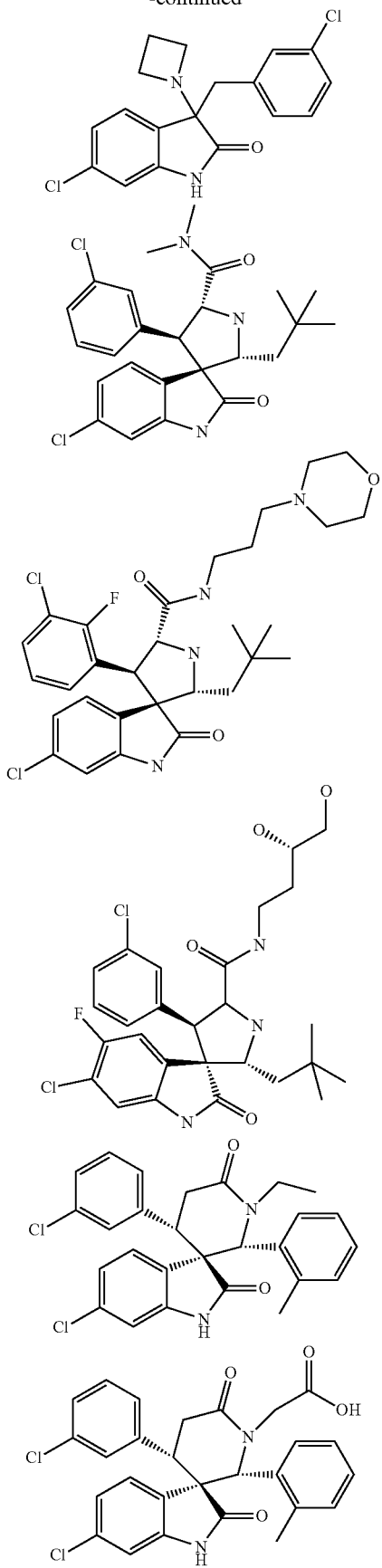
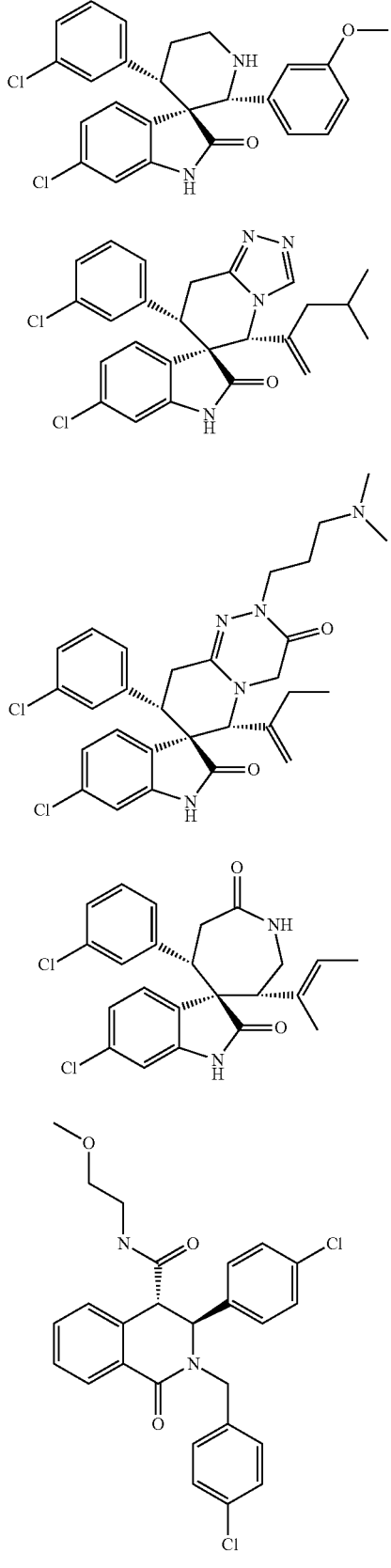

27
-continued
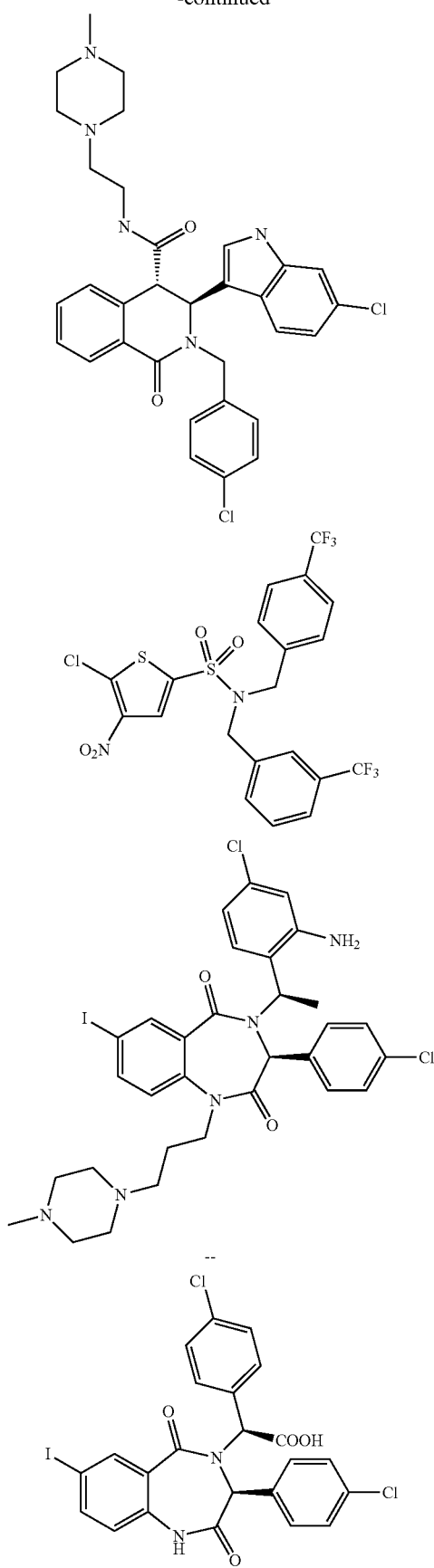
28
-continued
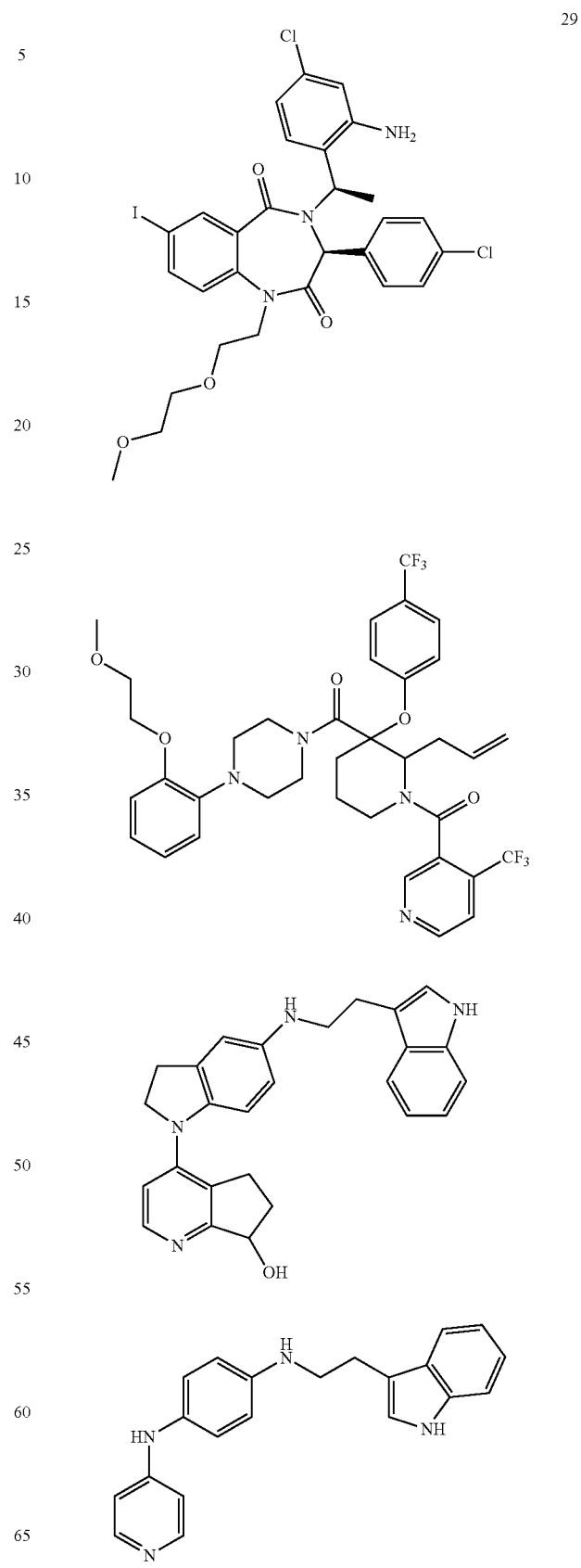

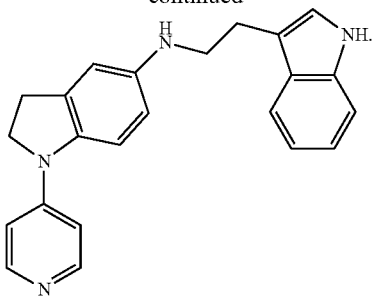

12. A method for preparing a vaccine against an influenza virus, characterized in that it comprises the production of an influenza virus by means of a method as claimed in claim 1.

13. A method for preparing a vaccine, characterized in that it comprises the production of a whole influenza virus by means of a method as claimed in claim 1 and the production of antigenic surface proteins using said whole influenza virus.

14. The method as claimed in claim 12, characterized in that the vaccine obtained comprises killed pathogens or live attenuated pathogens.

15. The method for producing an influenza virus as claimed in claim 4, characterized in that the influenza virus is an influenza subtype A viruses of the H1N1, H2N2, H3N2, H4N2, H4N6, H5N1, H5N2, H7N7 and H9N2 strains.

16. The method for producing an influenza virus as claimed in claim 15, characterized in that the influenza virus is the A H3N2 virus.

17. The method for producing an influenza virus as claimed in claim 1, characterized in that it comprises the inactivation of the virus harvested in step d.

* * * * *